(12) United States Patent
Gálvez Gámiz

(10) Patent No.: US 12,427,306 B2
(45) Date of Patent: Sep. 30, 2025

(54) ELECTROPHYSIOLOGY SYSTEM

(71) Applicant: Manuel Gálvez Gámiz, Barcelona (ES)

(72) Inventor: Manuel Gálvez Gámiz, Barcelona (ES)

( * ) Notice: Subject to any disclaimer, the term of this patent is extended or adjusted under 35 U.S.C. 154(b) by 498 days.

(21) Appl. No.: 17/927,806

(22) PCT Filed: May 26, 2021

(86) PCT No.: PCT/EP2021/064119
§ 371 (c)(1),
(2) Date: Nov. 25, 2022

(87) PCT Pub. No.: WO2021/239848
PCT Pub. Date: Dec. 2, 2021

(65) Prior Publication Data
US 2023/0211155 A1 Jul. 6, 2023

(30) Foreign Application Priority Data
May 27, 2020 (EP) .................................... 20382451

(51) Int. Cl.
*A61N 1/20* (2006.01)
(52) U.S. Cl.
CPC ..................................... *A61N 1/205* (2013.01)
(58) Field of Classification Search
CPC ............................. A61N 1/0476; A61N 1/205
See application file for complete search history.

(56) References Cited

U.S. PATENT DOCUMENTS

| | | |
|---|---|---|
| 2013/0165916 A1 | 6/2013 | Mathur et al. |
| 2014/0266235 A1 | 9/2014 | Mathur |
| 2015/0265834 A1 | 9/2015 | Glukhovsky et al. |
| 2018/0318583 A1 | 11/2018 | McBride |

FOREIGN PATENT DOCUMENTS

KR 20110114974 A 10/2011

OTHER PUBLICATIONS

International Search Report issued on Jul. 14, 2021, in corresponding International Application No. PCT/EP2021/064119, 15 pages.

*Primary Examiner* — Amanda K Hulbert
(74) *Attorney, Agent, or Firm* — Maier & Maier, PLLC

(57) ABSTRACT

An electrophysiology system for removing an excess of ions from a predetermined area of a patient's body. The system includes an electric signal source configured to generate an electric signal, a plurality of electric channels connected to the electric signal source and a controller. Each channel includes an electric signal emitter and an electric signal receiver. A signal path may be created therebetween. Such signal path is to be passed through the lymphatic system of a patient to move an excess of ions. The controller is configured to operate in an operational mode. The controller operating in the operational mode is configured to: send a first electric test signal, measure the first electric test signal, compare the measured first electric test signal and the sent first electric test signal, indicate the result of the comparison and apply a first treatment electric signal based on the comparison.

20 Claims, 4 Drawing Sheets

ELECTROPHYSIOLOGY SYSTEM

RELATED APPLICATIONS

This application claims the benefit of the European Patent Application EP 20 382 451.1 filed on May 27, 2020.

FIELD

The present disclosure is related to electrophysiology systems, more specifically to electrophysiology system for removing an excess of ions from a predetermined area of a patients body.

BACKGROUND

The lymphatic system comprises a plurality of lymph vessels which function as a biological drainage. The lymph vessels may interchange fluids with the body cells and transport nutrients and/or biological waste from/into the blood.

Some body cells, e.g. neurons, may be damaged after an accident or due to certain diseases, e.g. an ictus, among other reasons. The damaged neurons are not operative, i.e. they can no longer perform a normal function. These damaged neurons may release ions such as sodium and/or potassium ions.

Such released ions may accumulate around neighbouring operative or healthy neurons, e.g. in the extracellular fluid that surrounds neighbouring healthy neurons, thereby producing a change in their normal polarity. The accumulated ions prevent the normal function of these neighbouring healthy neurons. These healthy neurons may be blocked by the accumulation of the released ions. Such blocked cells may not interact with each other, i.e. they are not able to send and/or receive signals. As a result, not only the damaged neurons but also the neighbouring cells are not able to function properly thereby functional diseases such as reduced mobility at certain parts of the body, e.g. limbs, may be aggravated.

Electrophysiology is the branch of physiology that studies the flow of ions in biological tissues. Electrophysiology systems or devices are known for measuring the electrical properties, i.e. the flow of ions, of biological cells and tissues. Examples of electrophysiology systems may be electrocardiography devices (ECG or EKG) to measure the electrical activity of the cardiac muscle, electroencephalography devices (EEG) to measure the electrical activity of the brain and electromyography devices (EMG) to measure the electrical activity of the muscles (EMG). The electrophysiology devices are generally used for measuring the electrical activity of a part of the body to detect pathologies or to monitor a health status of this part of the body.

Electrostimulation devices may be used to stimulate a part of a body by applying an electric current. Examples of electrostimulation devices may be Transcutaneous Electrical Nerve Stimulation (TENS) or Electrical Muscle Stimulation (EMS). The Transcutaneous Electrical Nerve Stimulation (TENS) devices use electric current to stimulate the nerves for therapeutic purposes such as reducing pain. Besides, Electrical Muscle Stimulation (EMS) devices use electric impulses for muscle contraction for strength training or as a rehabilitation tool. Electrostimulation devices are thus used for therapeutic purposes.

However, such electrostimulation devices are used to simulate the function of the nervous system and not to act upon the lymphatic system and/or the lymphatic vessels. Additionally, TENS and EMS are usually designed to operate at currents having an intensity greater than 1 mA. Intensities greater than 1 mA may be appropriate for stimulating the nervous system but not for other purposes. Furthermore, these systems promote the accumulation of ions which contribute to cell blocking.

In conclusion, it would be desirable to provide a device that removes an excessive ion concentration in the extracellular fluid around healthy neurons in an effective and reliable way.

SUMMARY

In a first aspect, an electrophysiology system for removing an excess of ions from a predetermined area of a patient's body is provided. The system comprises an electric signal source configured to generate an electric signal, a plurality of electric channels connected to the electric signal source and a controller. Each channel comprises an electric signal emitter configured to send an electric signal generated by the electric signal source to a patient's body and an electric signal receiver configured to receive the electric signal sent from the electric signal emitter flowing through a part of the patient's body. Thus, a signal path may be created therebetween, wherein such signal path is to be passed through the lymphatic system of the patient to move an excess of ions. The controller is configured to operate in an operational mode. The operational mode comprises: sending a first electric test signal to the patient's body from the signal emitter of a first predetermined channel, measuring the first electric test signal received by the signal receiver of the first predetermined channel of the plurality of electric channels, comparing the measured first electric test signal and the sent first electric test signal, indicating the result of the comparison; and applying a first treatment electric signal to the patient's body based on the comparison from the electric signal emitter of the first predetermined channel.

The use of an electrophysiology system according to this disclosure, enables removing the excess of ions from a region where the cells are blocked due to a change in their normal polarity. Applying the first treatment electric signal to the extracellular fluid around healthy cells, e.g. healthy neurons, may remove an excess of ions surrounding these healthy cells and the difference of polarity between the cells and the extracellular fluid may be reduced. Consequently, the blocked cells may recover the normal functioning i.e. they may receive and send signals for intercellular communication. The electrophysiology system may thus restore the normal functioning of neurons blocked by an excess of ions released by damaged neurons. Moreover, the removed ion excess may be moved along the lymphatic system e.g. until the excess is drained through the blood.

In this disclosure, an electrophysiology system is used to describe medical devices configured to measure an electric signal flowing through a part of a patient's body.

Contrary to other electrophysiology systems, such as ECG or EEG or EMG, the electrophysiology system according to this disclosure is configured to apply an electric signal to the patient's body for treatment purposes. Furthermore, the electrophysiology system according to this disclosure measures an electric signal sent by the electric signal emitter and not the electric activity of a part of the patient's body.

In addition, contrary to the electrostimulation devices, such as TENS or EMS, the electrophysiology device according to this disclosure activates blocked neurons by removing an excess of ions surrounding these blocked neurones and transporting these removed ions through the lymphatic system. In addition, the electrophysiology system according to this disclosure comprises an electric signal receiver to measure the electric signal received from the electric signal emitter.

Therefore, a patient having a reduced functioning such as limited limb movement, may partially recover the loss of mobility aggravated by the blocked cells. That is, the electrophysiology system of this disclosure enables unblocking healthy cells by restoring their natural polarity conditions by removing the extra charge added by surplus of ions.

In addition, the use of a plurality of channels provides a more efficient and reliable system because they enable treating more than one area at the same time. Time of treatment may thus be reduced. Furthermore, having a system with a plurality of channels enables determining whether a signal path is interrelated with at least a further path.

Moreover, by having a controller configured to compare (and indicate) the difference between the test signal sent by the electric signal emitter and the test signal received by the electric signal receiver useful information may be obtained. Comparing the received test signal and the sent test signal may provide information from the health status of the part of the body's patient between the electric signal emitter and the electric signal receiver. Indeed, depending on the difference it may be indicative of a wrong positioning of the signal emitter and/or receiver and/or a presence of interrelated signal paths when applying a treatment electric signal. In addition, the comparison may confirm that there is a disease or a zone comprising extracellular fluid with an excess of ions surrounding healthy neurons between the electrical signal emitter and the electrical signal receiver.

In an example, the controller may be configured to operate at operational mode in a second predetermined channel and thus, the system may start operating at a second channel automatically i.e. without stopping the process and initializing the system for another predetermined channel. Therefore, the overall treatment session time may be substantially reduced. In addition, it also facilitates treating at least two different zones without removing and replacing the signal emitter(s) and receiver(s) from the patient's skin. That is, the plurality of emitters/receivers of the plurality of electric channels may be arranged at the beginning of the session.

In an example, applying a first treatment electric signal may comprise sending the first treatment electric signal from the electric signal emitter and measuring the first electric signal received by the signal receiver. The sent first treatment electric signal and the received first treatment electric signal may be compared. The comparison may indicate the health status of the part of the body between the electric signal emitter and the electric signal receiver. Using several comparisons during a period of time may indicate an evolution of the health status.

In an example, the controller may be configured to substantially simultaneously apply the first treatment electric signal and the second treatment electric signal. For example, the first treatment electric signal and the second treatment electric signal may collaborate to treat the same area of the patient's body.

Alternatively, or additionally, the controller may be configured to apply the second treatment electric signal with a predetermined delay after the first treatment electric signal. Therefore, interferences between the treatment electric signals may be prevented.

In an example, the controller may be further configured to operate in a preliminary mode. The controller operating in the preliminary mode is configured to send a query electric signal from the signal emitter of a predetermined electric channel of the plurality of electric channels, to measure the query electric signal received by the electric signal receivers of the remaining electric channels of the plurality of electric channels and to identify the electric signal receivers with a measured query electric signal lower than a predetermined portion of the sent query electric signal.

By using a controller configured to identify (part of) the query signal received by the signal receivers may determine before starting the treatment a zone comprising extracellular fluid with an excess of ions surrounding healthy cells and/or a presence of interrelated lymphatic paths that may cause interrelated electric paths when applying several treatment electric signals. Operating in the preliminary mode may provide data to determine a specific treatment on a specific zone of a patient.

In an example, the electrophysiology system may further comprise a user interface and the controller may be configured to apply a signal selected via a user interface. The use of a user interface allows the user to visualize the signals and also to modify their parameters before being applied, the treatment may therefore be more efficient. In an example, the user interface may display electric signals in real time.

In an example, the electric signal source may be configured to generate electric signals having an intensity equal to or lower than 300 µA. Contrary to greater intensities, e.g. the typical operating intensities of TENS or EMS, the electric signals having an intensity equal to or lower than 300 µA enable restoring the polarity of cells that accumulate a charge excess, i.e. blocked cells, and so, a normal functionality of such cells may be recovered.

In an example, the electric signal emitter and/or the electric signal receiver may comprise an electrode pad comprising a pressing element to transmit and/or receive an electric signal to or from the patient. When the electrode pad is arranged on the patient's skin, the pressing element exerts a pressure onto the skin to increase the electrical transmission between the skin and the electrode pad. The pressing element may comprise a protrusion on the side to be arranged on the patient's skin. The protrusion may reduce the area of contact of the pressing element with the patient's skin. As a result, the pressure exerted by the pressing element onto the patient's skin may be further increased and the electric signals may flow better through the pressing element to the patient's skin. Consequently, the electric signals may be more precisely applied and electric signal losses may be reduced. An electrical signal may thus be precisely applied to the lymphatic system, in particular, an electrical signal having an intensity equal or lower than 300 µA. The protrusion may also increase the sensitivity of the pressing element, and, consequently, of the electric signal receivers and/or of the electric signal emitters.

In an example, the pressing element may comprise a coupling pin at an opposite side of the protrusion for removably coupling the electrode pad to a socket connected to an electric wire. The use of a coupling pin enables replacing only the electrode pad (instead of the whole electric signal emitter/receiver comprising the socket). The system is therefore cost efficient and environmentally friendly as the amount of waste is reduced.

In an example, the electrode pad may comprise a ring comprising electrically conducting gel around the pressing element to further reduce the electric signal losses.

In an example, the system may further comprise a storage element to store the sent electric signals and the measured electric signals. Using a memory device allows not only monitoring the evolution of each patient but also clinical trials. Using data stored in the storage element may also help to select a specific treatment and to control the evolution of the treatment.

In a further aspect, an electrode pad for an electrophysiology system is provided. In some examples, the electrode pad may be used in an electrophysiology system according to any of the examples herein disclosed. In some examples, the electrode pad may be used in other electrophysiology systems, such as ECG or EMG. The electrode pad is thus configured to receive an electric signal.

The electrode pad may comprise a pressing element to receive an electric signal from the patient's body. In some examples, the pressing element may be configured to transmit and to receive an electric signal to and from the patient's body. The pressing element may comprise a protrusion on the side to be arranged on the patient's skin. The electrode pad may further comprise a base supporting the pressing element. The pressing element may be at least partially embedded in the base. The base may comprise a side with an adhesive layer to adhere the electrode pad to the patient's skin.

The protrusion may extend substantially perpendicular to the base. When the electrode pad is applied onto the patient's skin, the protrusion extends perpendicular to the patient's skin to concentrate the transmission of the electric signal between the electrode pad and the patient's skin.

In some examples, the protrusion may have a diameter of about 1-10 mm, specifically about 2-6 mm. The electric signal may thus be precisely transmitted between the pressing element and the patient's skin. In some examples, the protrusion may extend from the pressing element about 1-10 mm, specifically about 1-5 mm.

In some examples, the base may comprise a ring around the pressing element comprising an electrically conducting gel.

In some examples, the pressing element may comprise a coupling pin at an opposite side of the protrusion for removable coupling the electrode pad to an electrode socket.

In yet a further aspect, a method for removing an excess of ions from a predetermined area of a patient's body is provided. The method may involve using the electrophysiology system according to any of the examples herein disclosed. The method may comprise arranging a plurality of electric signal emitters and receivers on the patient's skin. The method may further comprise selecting an operational mode, wherein the operational mode comprises generating a first electric test signal, sending the first electric test signal from a signal emitter of a first channel of a plurality of electric channels, measuring the first electric test signal received by a signal receiver of the first channel of the plurality of electric channels, comparing the measured first electric test signal and the sent first electric test signal, indicating the result of the comparison, and applying a first treatment electric signal based on the comparison from the electric signal emitter of the first predetermined channel.

In some examples, the operational mode may further comprise indicating the result of the comparison.

In some examples, applying a first treatment electric signal may comprise sending the first treatment electric signal from the electric signal emitter of the first predetermined channel and measuring the first treatment electric signal received by the signal receiver of the first predetermined channel.

In some examples, the operational mode may further comprise sending a second electric test signal from the signal emitter of a second predetermined channel of the plurality of electric channels, wherein the second predetermined channel is different from the first predetermined channel; measuring the second electric test signal received by the signal receiver of the second predetermined channel of the plurality of electric channels; comparing the measured second electric test signal and the sent second electric test signal; indicating the result of the comparison; and applying a second treatment electric signal based on the comparison from the electric signal emitter of the second predetermined channel.

In some examples, the method may comprise simultaneously applying the first treatment electric signal and the second treatment electric signal. In some examples, the method may comprise delaying the second treatment electric signal after the first treatment electric signal.

In some examples, the method may further comprises selecting a preliminary mode before the operational mode. The preliminary mode may comprise sending a query electric signal from the signal emitter of a predetermined electric channel of the plurality of electric channels, measuring the query electric signal received by the electric signal receivers of the remaining electric channels of the plurality of electric channels, and identifying the electric signal receivers with a measured query electric signal lower than a predetermined portion of the sent query electric signal.

BRIEF DESCRIPTION OF THE DRAWINGS

Particular embodiments of the present device will be described in the following by way of non-limiting examples, with reference to the appended drawings, in which.

DETAILED DESCRIPTION

Figure 1:
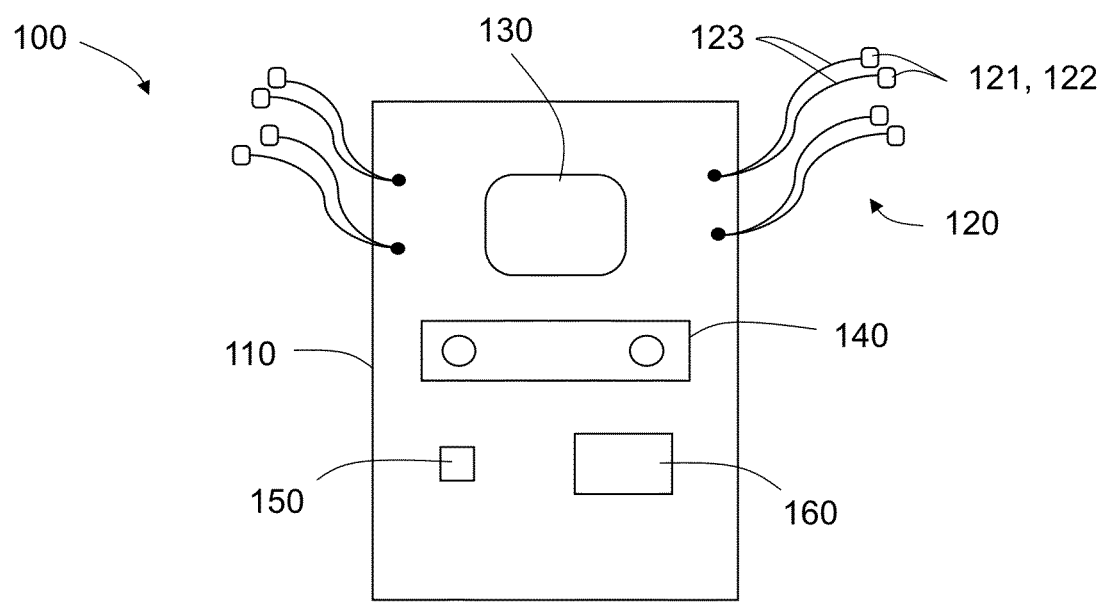
FIG. 1 schematically illustrates an electrophysiology system according to an example.

To clarify some of the terms used throughout the present description and claims, some definitions will be given.

The term "normal polarity" is to be understood as the polarity of a cell under usual conditions i.e. in absence of an excess of ions.

The term "normal functioning" is to be understood as the conventional operating performance.

The term "electric channel" is to be understood as the portion of an electric circuit created between an electric signal emitter and an electric signal receiver in which the electric current flows inside the electrophysiology system, i.e. out of the patient. The electric channel is thus the part of the electric circuit that flows from the electric signal source to an electric signal emitter through an electrical wire, and from the electric signal receiver to the electric signal source through an electrical wire.

The term "signal path" is to be understood as the portion of an electric circuit created between an electric signal emitter and an electric signal receiver wherein the electric current flows through inside a patient, more specifically through the lymphatic system of a patient. Therefore, the electric circuit comprises the electric channel and the signal path.

The term "interrelated signal paths" is to be understood as at least two electric signal paths sharing or having at least a branch in common. Therefore, part of the electric current of one electric channel flows into the other(s) signal path(s) which may be explained as electric signal losses.

The term "preliminary mode" is to be understood as a diagnosis stage of the electrophysiology system wherein the characteristics of the patient e.g. the presence of pathologies, are checked.

The term "operational mode" is to be understood as a treatment stage comprising using data from an electric signal emitter and from an electric signal receiver of the same electric channel to generate a treatment electric signal and applying this treatment electric signal to the patient's body. This data may indicate a health status of the zone between the electric signal emitter and the electric signal receiver.

The term "query signal" is to be understood as an electric signal having a minimum intensity that is used at a preliminary or diagnosis stage. A query signal may be used to determine parts of the body wherein the extracellular fluid surrounding cells has an excess of ions, and/or interrelated lymphatic paths that may cause interrelated electric paths when applying a treatment electric signal in the operational mode.

The term "test signal" is to be understood as an electric signal that is used at the operational stage. A test signal may be used to ensure the correct positioning of signal emitters/receivers, to determine the presence of interrelated signal paths, to confirm an area having cells surrounded by an excess of ions between the emitter and the receiver and also to control the evolution of the patient.

The term "treatment signal" is to be understood as an electric signal configured to remove an excess of ions from the extracellular fluid around a cell of a predetermined area of the patient thereby restoring the normal polarity and functionality of blocked cells. The intensity of a treatment signal may be greater than the intensity of a test signal.

FIG. 1 depicts an electrophysiology system 100 which may comprise a housing 110, a controller 160, an electric signal source 150 and a plurality of electric channels 120 connected to the electric signal source 150 and/or the controller 160.

The controller 160 may operate in an operational mode according to any of the examples herein disclosed. The controller may further operate in a preliminary mode according to any of the examples herein disclosed.

The housing 110 may protect the elements contained therein. In an example (not shown), the housing 110 may comprise wheels to facilitate its movement.

Each electric channel 120 of the plurality of electric channels may comprise at least an electric signal emitter 121 configured to send an electric signal generated by an electric signal source and an electric signal receiver 122 configured to receive an electric signal. In addition, each channel 120 may comprise at least two wires 123 to connect the electric signal emitter 121 and the electric signal receiver 122 to the electric signal source 150 and to the controller 160, respectively. The electric signal emitter(s) and receiver(s) may be configured to be arranged in contact with the patient's skin e.g. they may comprise an electrode pad having a layer with adhesive material, and may thus transmit signals to/from the patient's skin.

In an example, the electrophysiology system 100 may comprise 28 electric channels. However, any other number of electric channels according to any of the disclosed examples may be used.

The electric signal source 150 may be configured to generate electric signals having an intensity equal to or lower than 300 µA. Alternatively, or additionally, the electric signal source 150 may be configured to generate electric signals having a voltage equal to or lower than 20 V, optionally lower than 15 V. In an example, the system 100 comprises an electric signal generator per each electric channel. The electric signal source 150 may be a DC signal source. The current generated by the electric signal source may be limited.

In an example, the electric signal source 150 may comprise a current-limiting element, e.g. resistive element or a resistor, that prevents generating signals having more than 500 µA. In an example, the electrophysiology system may comprise a current-limiting circuit comprising an operational amplifier i.e. an op-amp. In an example, the electrophysiology system may comprise a current-limiting software configured to switch off the electric signal source in case the generated current is above 300 µA. In an example, the electrophysiology system may comprise any combination of these systems to limit the current generated by the electric signal source.

The electric signal source may be configured to simultaneously generate several electric signals for different electric channels. For example, the electric signal source may comprise a plurality of modules associated with the electric channels. Each of these modules may generate an electric signal independent from the other modules. As a result, the electric signal receiver of each electric channel may receive the electric signal generated by one module of the electric signal source.

As shown in FIG. 1, the electrophysiology system 100 may also comprise a user interface 130 e.g. a tactile screen. The user interface 130 may be configured to display at least an electric signal in real time, e.g. an emitted signal or a received signal. In examples wherein several electric signals are being emitted and/or received simultaneously, the user interface may also be configured to display a plurality of signals. In such examples, the user interface 130 may also be configured to associate each signal of the plurality of signals with its respective electric channel 120 and/or electric signal emitter/receiver 121, 122.

The user interface 130 may be further configured to display an electric signal before being emitted by an electric signal emitter. In some examples, a confirmation from the user may be required before applying such displayed signal and thus, the controller may be configured to prevent the emission of an electric signal until a confirmation is received. The user interface 130 may comprise or may display a confirmation button (not shown) for receiving such confirmation.

The user interface 130 may also comprise or may display a disregard button to prevent applying electric signals not approved by the medical staff. Therefore, it may be ensured that a qualified medically staff has validated the signal before being emitted.

In some examples, the electrophysiology system 100 may comprise a panel 140 having a validation button, a disregard button and at least an adjusting element. The adjusting element may be configured to modify, i.e. increase or decrease, the value of at least a parameter of the displayed electric signal(s). The parameters of an electric signal may comprise voltage, current intensity, duration of the pulse, etc.

In an example, the adjusting element(s) may be arranged at the user interface 130. The electric signals may therefore be adjusted by medical staff before being applied to the patient, which provides a more personalized and more efficient treatment. The adjusting element may be for example a button.

The user interface may also be configured to depict statistical data related to patient's progress e.g. during the treatment session and/or after several treatment sessions.

The electrophysiology system 100 may further comprise a storage element (not shown) for storing data such as the electric signals sent by the electric signal emitter(s) and the electric signals received by the electric signal receivers. By storing the electric signals, the progress of the patient may be monitored not only during the session but also during the whole treatment. The stored data may also be used to create a statistical data base for research, medical trials and/or clinical studies.

The controller 160 of the electrophysiology system 100 may be configured to control all the processes carried out by the electrophysiology system. To that end, the controller may be connected at least to the signal source(s) and the user interface via a wireless communication system e.g. Wi-Fi, Bluetooth, etc. In an alternative example, a wired communication system may be used.

In some examples, the controller 160 may be configured to operate with a single electric channel 120, i.e. the functioning may include only an activated channel. In other examples, the controller 160 may be configured to operate with a plurality of electric channels. In such examples, the controller may be configured to activate one or more electric channels simultaneously, that is, sending a respective electric signal via the electric signal emitter of each electric channel.

Figure 2:
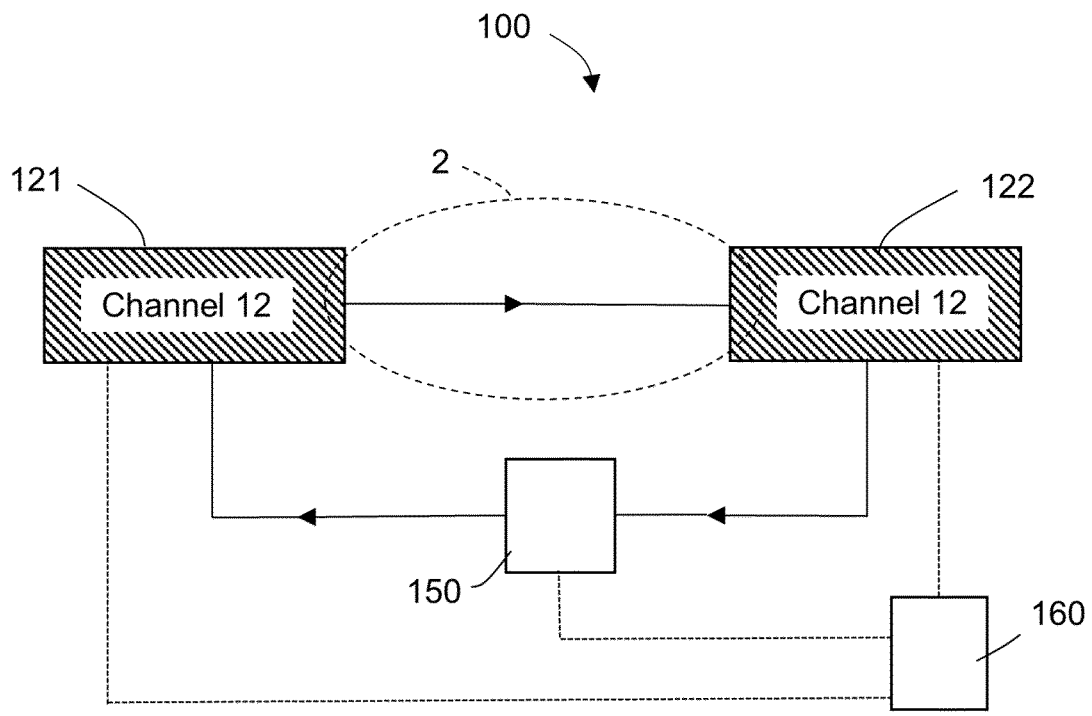
FIG. 2 schematically a simplified diagram of an electrophysiology system operating with a single electric channel.

FIG. 2 depicts a simplified diagram of an electrophysiology system wherein the controller is configured to operate with a single electric channel. The figure shows a signal emitter 121 and a signal receiver 122 of a predetermined channel e.g. channel 12; a controller 160, and a signal source 150.

The controller 160 may be configured to send a control signal (see dashed line) to the electric signal source 150. The signal source may then generate an electric signal according to the parameters predefined by the controller e.g. encoded in the control signal. The generated signal may then be sent to the signal emitter 121 which may be arranged on the patient's skin. In this figure, the signal emitter 121 is electrically connected to the electric signal source.

The generated signal may then be transmitted into the patient's body and may flow therein from the signal emitter 121 to the signal receiver 122. A signal path 2 may thus be created. A signal path 2 is the trajectory of an electric signal or the portion of the circuit that flows inside the patient's body. When the electric signal is received by the receiver, the resulting data may be sent to the controller. The received data may be used to evaluate the change of the electric signal when passing through the body e.g. due to the resistance, a disease or losses due to interrelated paths. Indeed, the electric signal received by the signal receiver may not be equal to the sent signal for instance due to interrelated paths, the impedance due to a certain disease, etc. In an example, the received data may be stored in a storage element. The signal receiver may be electrically connected to the electric source.

Figure 3:
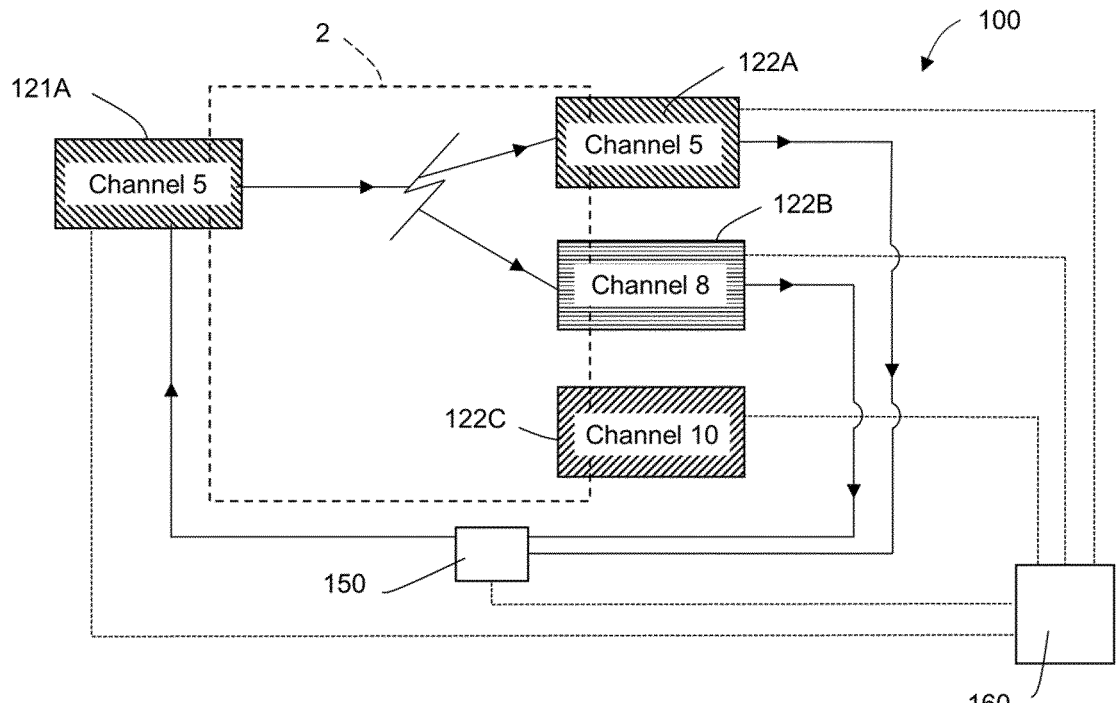
FIG. 3 schematically a simplified diagram of an electrophysiology system operating with a plurality of electric channels.

FIG. 3 shows a simplified diagram of an electrophysiology system 100 wherein the controller is configured to operate with a plurality of channels. In an example, only a receiver or an emitter of a particular signal may be used.

In the example of this figure, the electrophysiology system 100 is configured to operate with three channels, more specifically with an electric signal emitter 121A and an electric signal receiver 122A of a predetermined channel, e.g. channel 5, and with two electric signal receivers 122B, 122C of two different channels e.g. channel 8 and channel 10, respectively. That is, the electric signal emitters 121B, 121C of channels 8 and 10 are not used in this example.

In this figure, the electric signal emitter 121A is electrically connected to the electric signal source 150. The electric signal receivers 122A, 122B and 122C of this figure are electrically connected to the electric signal source 150.

In one example, each of the electric signal receivers 122A, 122B and 122C may be electrically connected to a different module of the electric signal source. These modules may be configured to independently generate an electric signal for different channels.

The generated electric signal may be transmitted into the patient's body and may flow therein from the signal emitter to the signal receiver 122A via an electric signal path 2. In the example of FIG. 3, the electric signal path 2 comprises two branches (see the arrows): a first branch that connects the electric signal emitter 121A with the electric signal receiver of its own channel i.e. the electric signal receiver 122A; and a second branch that connects the electric signal emitter 121A and the electric signal receiver 122B e.g. of channel 8. Therefore, in this example, the electric signal sent by the signal emitter 121A is received by two electric signal receivers 122A, 122B from two different channels which may be indicative of the presence of at least two interrelated channels for instance channel 5 and channel 8. However, no signal is received by electric signal receiver 122C e.g. because there is no interrelated electric path carrying electric current from emitter 122A to electric signal receiver 122C.

Monitoring a plurality of receivers may provide information to the medical staff i.e. useful information may also be extracted from electric signal receivers wherein no electric signal is received. For instance, the medical staff may modify the treatment depending on the obtained results.

The controller may then receive the data from each electric signal receiver. Afterwards, the controller may identify the electric signal receivers in which an electric signal is registered and may store the data in a storage element. Optionally, the controller may be configured to display via the user interface, the value of the electric signal upon being received by the electric signal receivers and/or the information regarding the electric channels.

Figure 4:
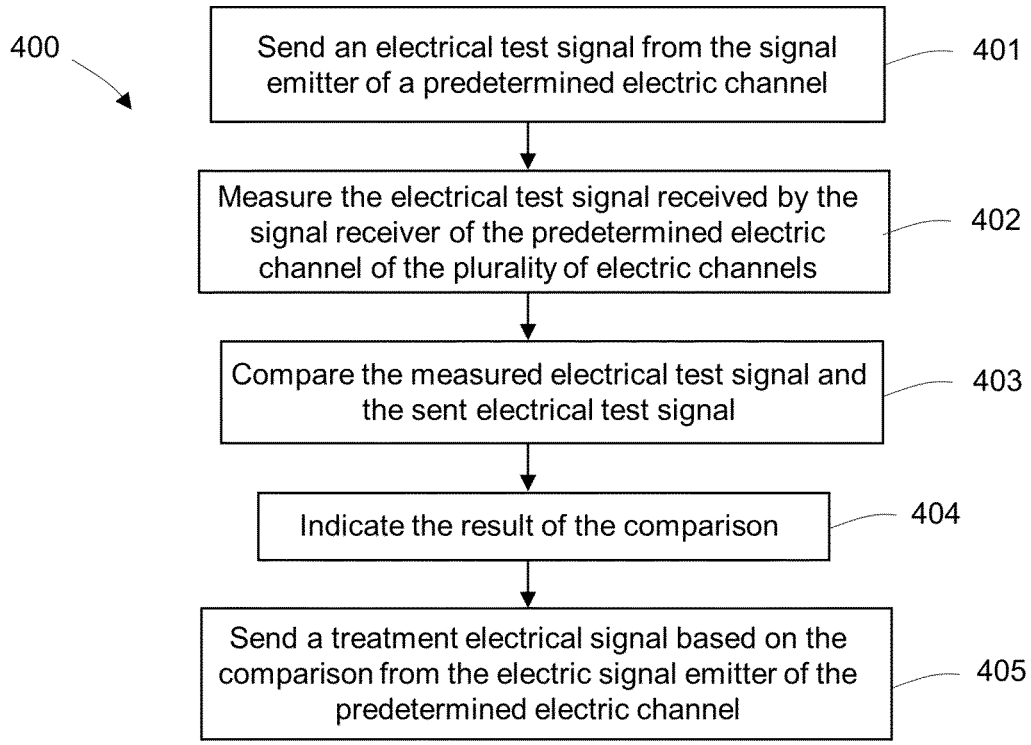
FIG. 4 illustrates a flow chart of the procedure of a controller operating in an operating mode according to an example.
Figure 5:
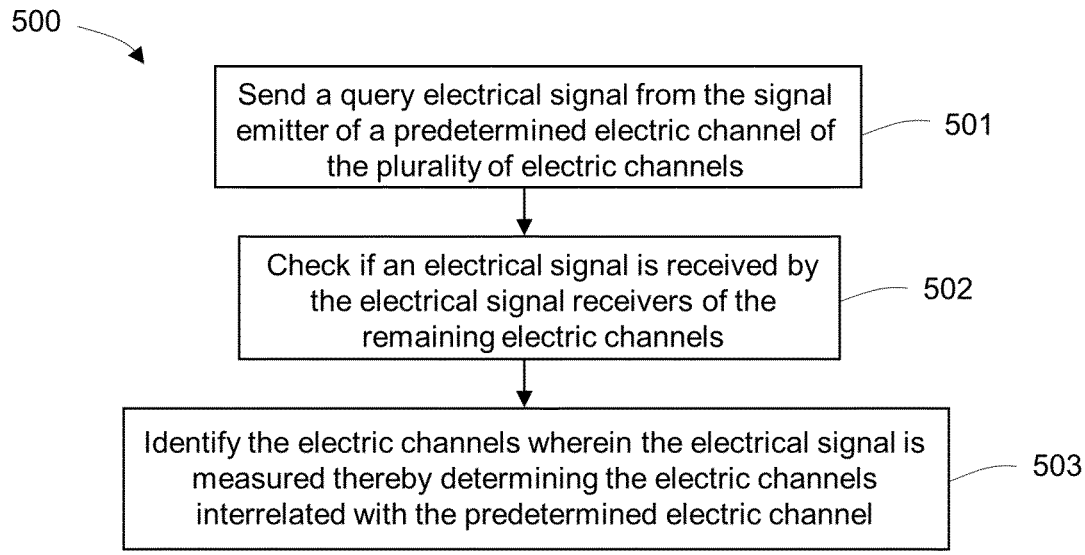
FIG. 5 illustrates a flow chart of the procedure of a controller operating in a preliminary mode according to an example.

In addition, the controller 160 may be configured to operate at least at two different modes: an operational mode (see FIG. 4) and a preliminary mode (see FIG. 5).

FIG. 4 depicts the implementation of the operational mode 400 according to an example.

At the operational mode, after arranging at least an electric signal emitter 121 and an electric signal receiver 122 of at least a predetermined channel, e.g. channel 12, on patient's skin, the operational mode may be initialized. Optionally, the electric signal emitter(s) and electric signal receiver(s) of each of the plurality of electric channels may be arranged on patient's skin before implementing the operational mode.

The controller may be configured to send, in block 401, a first electric test signal from the signal emitter of a first predetermined channel, e.g. channel 12, after being generated by an electric signal source. The first electric test signal may have an intensity lower than 300 µA, specifically lower than 100 µA, and more specifically lower than 50 µA.

The first electric test signal may flow across the patient's body, e.g. through specific lymphatic vessel, until it reaches the electric signal receiver of the predetermined channel, e.g. channel 1, thereby creating a signal path. The controller may then measure, in block 402, the electric test signal received by the signal receiver of the first predetermined channel. Afterwards, the controller may indicate, in block 403, the result of such comparison, for instance, by displaying it via the user interface.

After passing through the patient's body, the electric test signal may be weakened and thus, the result of the comparison may indicate the test signal difference. For example, the current intensity received by the electric signal receiver may be lower than the current intensity sent by the electric signal emitter.

In some examples, the loss degree may be indicative of a disease or presence of interrelated signal paths.

In some examples, the intensity loss degree may indicate the presence of interrelated signal paths, that is, part of the electric test signal flows through other lymphatic vessels and thus, is not received by the signal receiver of the same channel. This may indicate that there are parallel electrical signal paths.

Additionally, or alternatively, the voltage loss degree between the receiver and the emitter of the same channel may be within a natural range i.e. due to the natural resistance of body. However, if the value is out of the tolerance range, it may be indicative of neurons having an excess of ions in their extracellular fluid.

In addition, the controller may then apply, in block 404, a treatment signal. The treatment signal may be generated by a signal source according to specific parameters e.g. a predefined voltage and/or current. In an example, a treatment signal may comprise an intensity of about 100-300 µA. In an example, a treatment signal may comprise an intensity of about 100-200 µA. The intensity of the treatment signal may be adjusted using intervals of 1 µA. In an example, a treatment signal may comprise a voltage of about 5-20 V, optionally about 5-15 V.

In an example, such parameters may be defined based on the performed comparison. For instance, if the comparison indicates that an excess of ions has been significantly removed then the intensity of the treatment signal may be reduced. Similarly, the duration of the signal may also be specified depending on the result of the comparison. For example, if the difference between the received and sent electric signal is out of a predetermined range it may indicate e.g. that the excess of ions is not entirely removed and thus, a longer application period may be required.

After generating a treatment signal in a signal source, the electric signal emitter of the predetermined channel may send the generated treatment signal to the patient's body. After passing through the body, the treatment signal may be received by the signal receiver of the (same) predetermined channel. Then the signal may be measured. The values of the parameters may be stored and/or displayed via the user interface.

In some examples, the controller 160 may be further configured to operate at operational mode in at least a second predetermined electric channel i.e. different from the first predetermined channel.

The controller may be configured to perform the same procedure of first predetermined electric channel, e.g. channel 12, for a second electric channel, e.g. channel 8. That is, after generating a second treatment signal, an electric signal emitter of a second predetermined channel may send such second electric test signal. In an example, the second treatment signal may equal to the first test signal. In another example, the second treatment signal may be different from the first test signal.

After receiving the second electric test signal in an electric signal receiver of the second predetermined channel, the controller may measure the second electric test signal. Then, the controller may compare the measured second electric test signal and the sent second electric test signal and may indicate the result of the comparison e.g. by displaying it via the user interface.

Additionally, the result of the comparison may be recorded in a storage element e.g. for statistical analysis, to control the evolution of the patient after each session, to remember the position of the signal emitter(s) and receiver(s), etc.

Finally, the controller may apply a second treatment electric signal. In an example, the second treatment signal may be equal to the first treatment signal. In an example, the second treatment signal may be different to the first treatment signal. Such second electric signal may be based on the performed comparison. Thus, the parameter values may be adjusted by the medical staff depending on the result. In an example, the controller may adjust the parameter values based on a plurality of treatment electric signals.

The operational mode may comprise using more than two predetermined channels as described above with respect to two electric channels, e.g. it may be implemented subsequently for all the electric channels of the electrophysiology system. The controller may therefore be configured to activate and deactivate each electric channel i.e. the signal emitter(s) and receiver(s) of each channel, without requiring medical staff intervention.

In an example, the controller may be configured to substantially simultaneously apply the first treatment electric signal and the second treatment electric signal. Therefore, different lymphatic vessels may be treated at the same time which reduces the time required for each session and increases effectiveness. The parameter of these treatment electric signals may be adjusted by the controller. Stored data or on-line data obtained from the signal emitters and from the signal receivers may be used for dynamically adjusted these treatment electric signals.

In an alternative example, the controller may be configured to apply the second treatment signal with a predetermined delay after the first treatment signal. The delay may be of about 0.5-6 seconds.

In cases wherein more than one electric channel is used, the controller may be configured to activate the one or more channels. That is, the operational mode or any other mode may be implemented for a plurality of electric channel(s) without intervention of the medical staff.

In addition to the operational mode, the controller may also be configured to operate in a preliminary mode. The implementation of such preliminary mode may be optional, and may depend e.g. on the patient's conditions and/or on the medical staff criteria.

The preliminary mode may be implemented before implementing the operational mode. In some examples, the preliminary mode may be implemented on the first session. In other examples, the preliminary mode may be implemented at each session before implementing the operational mode.

Information provided to the medical staff by the electrophysiology system when the controller is operating in the preliminary mode may be used to define a treatment.

FIG. 5 depicts the implementation of the preliminary mode 500.

During preliminary mode, the controller may be configured to send, in block 501, a query signal from the signal emitter of a predetermined electric channel e.g. the emitter of channel 5. The query signal may have a voltage lower than 10 V, specifically lower than 5 V. In an example, the query signal may have a current intensity lower than 300 µA, more specifically lower than 200 µA.

After passing through the patient's body, the query signal may be received by more than one electric signal receivers i.e. not only by the electric signal receiver of the predetermined channel. The controller may then measure, in block 502, the query electric signal received by the electric signal receivers at the remaining electric channels, i.e. the other electric channels. The controller may then identify, in block 503, the electric signal receivers wherein a portion of the query signal is measured.

The preliminary mode may be used not only to detect diseases but also to identify channels interrelated with the predetermined channel. For example, the signal emitter of channel 5 may send a query signal and part of that signal may be received at the signal receivers of channels 8 and 10.

As mentioned in relation to FIG. 1, the electrophysiology system 100 may comprise a plurality of electric signal emitter(s) and receiver(s).

Figure 6A:
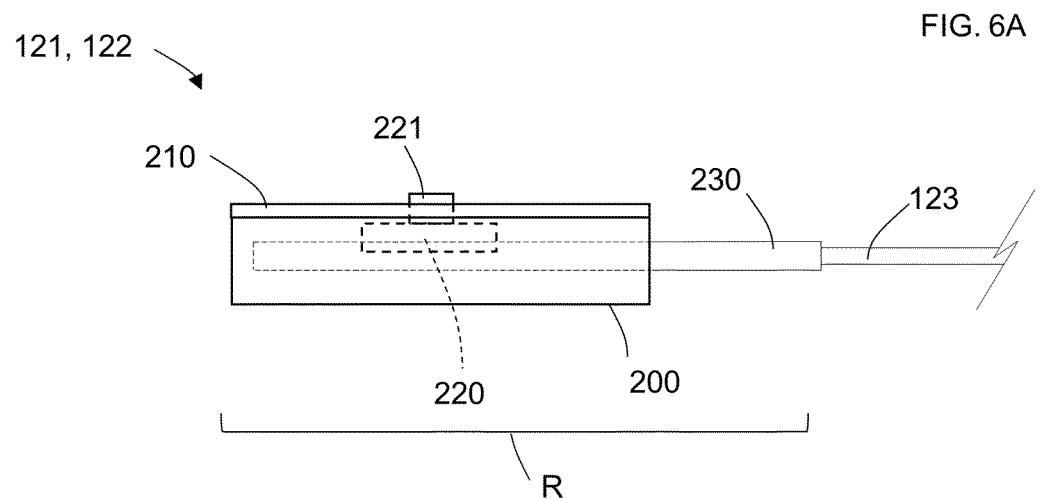
FIG. 6A schematically illustrates an electric signal emitter/receiver according to an example.
Figure 6B:
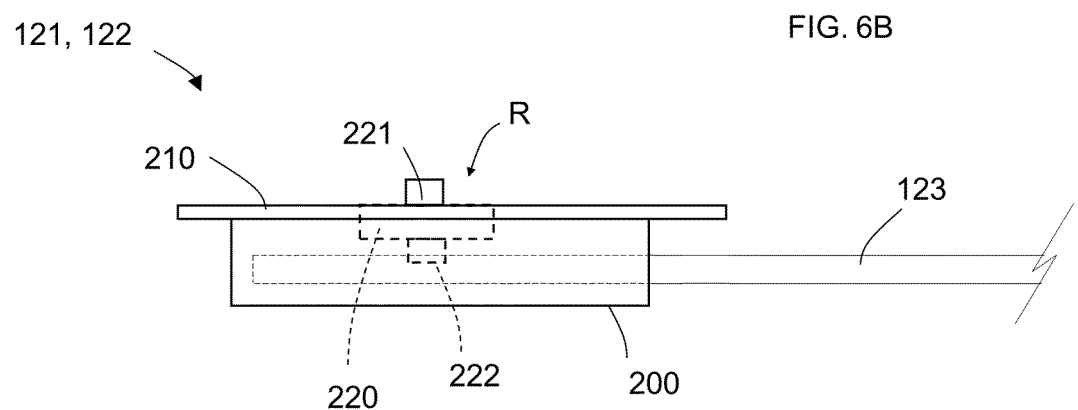
FIG. 6B schematically illustrates an electric signal emitter/receiver according to another example.

FIG. 6A and FIG. 6B show two examples of an electric signal emitter 121 or receiver 122 comprising an electrode pad 200.

In these figures, the electrode pad is depicted as forming part of an electrophysiology system according to this disclosure, however, the electrode pad according to these figures may also be used in other types el electrophysiology systems, such as ECG or EMG.

Each electric signal emitter(s) 121 and receiver(s) 122 may comprise an electrode pad 200 comprising an adhesive layer 210 to adhere the signal emitter/receiver to the patient's skin. The electric signal emitter(s) and receiver(s) may also comprise a removable cover sheet (not shown) arranged on the adhesive layer to protect the adhesive material until its use.

The electrode pad 200 may further comprise a pressing element made of a conductive material e.g. metal, that can transmit an electric signal into and from the patient's body. Such pressing element 220 may comprise a protrusion 221 on the side to be arranged on the patient's skin. In an example, the protrusion may have a diameter of about 1-10 mm, specifically about 2-6 mm. The protrusion may extend from the pressing element about 1-10 mm, specifically about 1-5 mm. Additionally, the electrode pad may be coupled to a wire 123 for coupling the conductive material to the signal source or to the controller.

In an example, a conductive gel be applied may on the patient's skin before arranging the electric signal emitter(s) or receiver(s). In an example, the adhesive layer 210 of electrode pad may also comprise a conductive gel for increasing the conduction of electric signals into/from the patient's body. In an example (not shown), the electrode pad may comprise a ring comprising an electrically conducting gel. The ring may be arranged around the pressing element.

The electric signal emitter/receiver 121, 122 may comprise a disposable portion that may be discarded after each use, i.e. session. Such disposable portion may be coupled to a fixed portion which is connected to the system thereby facilitating the removal of the disposable part and thus the overall process.

FIG. 6A depicts an example of an electric signal emitter/receiver 121, 122 having a removable socket R. In such example, the electric signal emitter/receiver 121, 122 comprise a wire coupling head 230 configured to receive a wire 123 which is connected to the electrophysiology system. In this example, the wire may comprise a coupling element (not shown) to couple the wire to the coupling head.

In some examples (see FIG. 6A), the electrode pad 200 and the wire coupling head may be removed together. In alternative examples (see FIG. 6B), only the electrode pad may be removable.

FIG. 6B depicts an example of an electric signal emitter/receiver 121, 122 having a removable electrode pad R. In such examples, the electric signal emitter/receiver 121, 122 comprise a coupling pin 222 for removably coupling the electrode pad to a socket. The coupling pin 222 may be arranged on the opposite side of the protrusion. In these examples, the socket may comprise a matching gap (not shown) having the external shape of the coupling pin for a secure fitting.

In an example, the electrophysiology system 100 may further comprise a security system e.g. resistive circuit, to control that the generated electric signals do not exceed a maximum predefined value.

The electrophysiology systems according to any of the examples herein disclosed may be a combination of electronic and computing means, the computing means may be a set of instructions, e.g. a computer program, and the electronic means may be any electronic circuit capable of implementing corresponding operating modes.

The computer program(s) may be embodied on a storage medium, e.g. a CD-ROM, a DVD, a USB drive, a computer memory or a read-only memory; or carried on a carrier signal e.g. on an electric or optical carrier signal.

The computer program(s) may be in the form of source code, object code, a code intermediate source and object code such as in partially compiled form, or in any other form suitable for use in implementing the operating modes according to any of the disclosed examples. The carrier may be any entity or device capable of carrying the computer program(s).

For example, the carrier may comprise a storage medium, such as a ROM, e.g. a CD ROM or a semiconductor ROM; or a magnetic recording medium, e.g. a hard disk. Further, the carrier may be a transmissible carrier such as an electric or optical signal, which may be conveyed via electric or optical cable or by radio or other means.

When the computer program(s) is/are embodied in a signal that may be conveyed directly by a cable or other device or means, the carrier may be constituted by such cable or other device or means. Alternatively, the carrier may be an integrated circuit in which the computer program(s) is/are embedded, the integrated circuit being adapted for performing, or for use in the performance of the proposed operating modes.

In use, the medical staff may firstly arrange the plurality of electric signal emitter and receivers on the patient's skin. In an example, all the electric signal emitter and receivers may be arranged. In another example, only the electric signal emitter and/or receiver of certain predetermined channel(s) may be arranged.

The electrophysiology system may then be selected, e.g. by medical staff, to operate at the preliminary mode. The preliminary mode may be optional and may be implemented e.g. during the first session or during the beginning of each session.

A query signal may be generated by the electric source and may then be transmitted to the patient's body via the electric signal emitter. The parameters of the generated query signal may be defined by the controller and, confirmed and/or modified by the medical staff. In another examples, the parameters of the generated query signal may be defined by the medical staff.

After passing through the patient's body, the query signal may be received at least by an electric signal receiver. According to the electric signal receiver(s) in which the query signal is received, the interrelated signal paths and/or zones of the body with pathologies may be identified, for instance, taken into account the information provided, e.g. displayed, via a user interface.

The electrophysiology system may then be switched into the operational mode e.g. by the medical staff. An electric test signal may be generated by the electric signal source e.g. according to the parameters defined by the controller or the medical staff or from a plurality of predetermined electric test signals. The test signal may be sent via an electric signal emitter of a predetermined channel and measured at an electric signal receiver of the same predetermined channel. According to or based on the information obtained from the voltage and/or intensity losses, the value of the parameters, etc. a treatment signal may be generated. The treatment signal may be applied though a predetermined signal path.

The treatment signal received at an electric signal receiver of the same predefined channel may be used to control a patient condition and to observe the evolution of the patient.

The process may be repeated for several channels simultaneously or successively. The medical staff may, in some examples, decide to use several electric channels simultaneously to increase the effectiveness of the treatment.

For reasons of completeness, various aspects of the present disclosure are set out in the following numbered clauses:

Clause 1. An electrode pad for an electrophysiology system comprising:
a pressing element to receive an electric signal from the patient's body;
a base supporting the pressing element having a side to be arranged on the patient's skin;
wherein the pressing element comprises a protrusion on the side to be arranged on the patient's skin.

Clause 2. The electrode pad according to clause 1, wherein the pressing element is configured to transmit an electric signal to the patient's body, specifically an electric signal having an intensity equal to or lower than 300 µA.

Clause 3. The electrode pad according to any of clauses 1-2, wherein the protrusion extends substantially perpendicular to the base.

Clause 4. The electrode pad according to any of clauses 1-3, wherein the base comprises an adhesive layer to adhere the electrode pad to the patient's skin.

Clause 5. The electrode pad according to any of clauses 1-4, wherein the protrusion comprises a diameter of about 1-10 mm, specifically about 2-6 mm.

Clause 6. The electrode pad according to any of clauses 1-5, wherein the protrusion extends from the pressing element about 1-10 mm, specifically about 1-5 mm.

Clause 7. The electrode pad according to any of clauses 1-6, wherein the base comprises a ring around the pressing element comprising an electrically conducting gel.

Clause 8. The electrode pad according to any of clauses 1-7, wherein the pressing element is at least partially embedded in the base.

Clause 9. The electrode pad according to any of clauses 1-8, wherein the pressing element comprises a coupling pin at an opposite side of the protrusion for removable coupling the electrode pad to an electrode socket.

Clause 10. The electrode pad according to any of clauses 1-8, wherein the electrode pad comprises an electric wire connected to the pressing element.

Clause 11. An electrophysiology system for removing an excess of ions from a predetermined area of a patient's body, the system comprising:
an electric signal source configured to generate an electric signal;
a plurality of electric channels connected to the electric signal source, wherein each channel comprises:
an electric signal emitter configured to send an electric signal generated by the electric signal source; and
an electric signal receiver configured to receive the electric signal sent from the electric signal emitter thereby creating a signal path that passes through the lymphatic system of a patient to move an excess of ions; and
a controller configured to operate in an operational mode, wherein the controller operating in the operational mode is configured to:
send a first electric test signal from the signal emitter of a first predetermined channel of the plurality of electric channels,
measure the first electric test signal received by the signal receiver of the first predetermined channel of the plurality of electric channels,
compare the measured first electric test signal and the sent first electric test signal,
indicate the result of the comparison; and
apply a first treatment electric signal based on the comparison from the electric signal emitter of the first predetermined channel.

Clause 12. The electrophysiology system according to clause 11, wherein apply a first treatment electric signal comprises:
send the first treatment electric signal from the electric signal emitter of the first predetermined channel, and
measure the first treatment electric signal received by the signal receiver of the first predetermined channel.

Clause 13. The electrophysiology system according to clauses 11 or 12, wherein, at the operational mode, the controller is further configured to:
send a second electric test signal from the signal emitter of a second predetermined channel of the plurality of electric channels, wherein the second predetermined channel is different from the first predetermined channel,
measure the second electric test signal received by the signal receiver of the second predetermined channel of the plurality of electric channels,
compare the measured second electric test signal and the sent second electric test signal,
indicate the result of the comparison; and
apply a second treatment electric signal based on the comparison from the electric signal emitter of the second predetermined channel.

Clause 14. The electrophysiology system according to clause 13, wherein the controller is configured to substantially simultaneously apply the first treatment electric signal and the second treatment electric signal.

Clause 15. The electrophysiology system according to clause 13, wherein the controller is configured to apply the second treatment electric signal with a predetermined delay after the first treatment electric signal.

Clause 16. The electrophysiology system according to any of clauses 11-15, wherein the controller is further configured to operate in a preliminary mode, wherein the controller operating in the preliminary mode is configured to:
  send a query electric signal from the signal emitter of a predetermined electric channel of the plurality of electric channels,
  measure the query electric signal received by the electric signal receivers of the remaining electric channels of the plurality of electric channels, and
  identify the electric signal receivers with a measured query electric signal lower than a predetermined portion of the sent query electric signal.

Clause 17. The electrophysiology system according to any of clauses 11-16, wherein the controller is further configured to activate one or more electric channels simultaneously thereby sending a respective electric signal via the electric signal emitter of each electric channel.

Clause 18. The electrophysiology system according to any of clauses 11-17, wherein the controller is configured to successively activate the electric channels.

Clause 19. The electrophysiology system according to any of clauses 11-18, further comprising a user interface and wherein the controller is configured to apply a signal selected via the user interface.

Clause 20. The electrophysiology system according to clause 19, wherein the user interface is configured to display the electric signals in real time.

Clause 21. The electrophysiology system according to any of clauses 11-20, further comprising a storage element to store the sent electric signals and the measured electric signals.

Clause 22. The electrophysiology system according to any of clauses 11-21, wherein the electric signal source is configured to generate electric signals having an intensity equal to or lower than 300 µA.

Clause 23. The electrophysiology system according to any of clauses 11-22, wherein the electric signal emitter and/or the electric signal receiver comprise an electrode pad comprising a pressing element having a protrusion on a side to be arranged on the patient's skin.

Clause 24. The electrophysiology system according to clause 23, wherein the pressing element comprises a coupling pin at an opposite side of the protrusion for removably coupling the electrode pad to an electrode socket.

Clause 25. The electrophysiology system according to clause 23 or 24, wherein the electrode pad comprises a ring comprising electrically conducting gel around the pressing element.

Clause 26. The electrophysiology system according to any of clauses 23-25, wherein the electrode pad is according to any of clauses 1-10.

Clause 27. The electrode pad according to any of clauses 1-10, wherein the electrode pad is configured to be used in the electrophysiology system according to any of clauses 11-22.

Clause 28. The electrode pad according to any of clauses 1-10, wherein the electrode pad is configured to be used in an electrocardiography device and/or an electroencephalography device and/or in an electromyography device.

Clause 29. A method for removing an excess of ions from a predetermined area of a patient's body, comprising:
  arranging a plurality of electric signal emitters and receivers on the patient's skin;
  selecting an operational mode, wherein the operational mode comprises:
    generating a first electric test signal;
    sending the first electric test signal from a signal emitter of a first channel of a plurality of electric channels;
    measuring the first electric test signal received by a signal receiver of the first channel of the plurality of electric channels;
    comparing the measured first electric test signal and the sent first electric test signal;
    applying a first treatment electric signal from the electric signal emitter based on comparing the measured first electric test signal and the sent first electric test signal.

Clause 30. The method according to clause 29, wherein the operational mode further comprises indicating a result of comparing the measured first electric test signal and the sent first electric test signal.

Clause 31. The method according to any of clauses 29-30, wherein applying a first treatment electric signal comprises sending the first treatment electric signal from the electric signal emitter of the first predetermined channel and measuring the first treatment electric signal received by the signal receiver of the first predetermined channel.

Clause 32. The method according to any of clauses 29-31, wherein the operational mode further comprises:
  sending a second electric test signal from the signal emitter of a second predetermined channel of the plurality of electric channels, wherein the second predetermined channel is different from the first predetermined channel;
  measuring the second electric test signal received by the signal receiver of the second predetermined channel of the plurality of electric channels;
  comparing the measured second electric test signal and the sent second electric test signal; and
  applying a second treatment electric signal based on the comparison from the electric signal emitter of the second predetermined channel.

Clause 33. The method according to clause 32, wherein the operational mode further comprises indicating a result of comparing the measured second electric test signal and the sent second electric test signal.

Clause 34. The method according to any of clauses 32-33, wherein the operational mode comprises simultaneously applying the first treatment electric signal and the second treatment electric signal.

Clause 35. The method according to any of clauses 32-34, wherein the operational mode comprises delaying the second treatment electric signal after the first treatment electric signal.

Clause 36. The method according to any of clauses 29-35, further comprising selecting a preliminary mode before the operational mode, wherein the preliminary mode comprises:
  sending a query electric signal from the signal emitter of a predetermined electric channel of the plurality of electric channels;
  measuring the query electric signal received by the electric signal receivers of the remaining electric channels of the plurality of electric channels, and
  identifying the electric signal receivers with a measured query electric signal lower than a predetermined portion of the sent query electric signal.

Although only a number of particular embodiments and examples have been disclosed herein, it will be understood by those skilled in the art that other alternative embodiments and/or uses of the disclosed innovation and obvious modifications and equivalents thereof are possible. Furthermore, the present disclosure covers all possible combinations of the particular embodiments described. The scope of the present disclosure should not be limited by particular embodiments, but should be determined only by a fair reading of the claims that follow.

The invention claimed is:

1. An electrophysiology system for removing an excess of ions from a predetermined area of a patient's body, the system comprising:
   an electric signal source configured to generate an electric signal;
   a plurality of electric channels connected to the electric signal source, wherein each channel comprises:
      an electric signal emitter configured to send an electric signal generated by the electric signal source to a patient's body; and
      an electric signal receiver configured to receive the electric signal sent from the electric signal emitter flowing through a part of the patient's body thereby creating a signal path that passes through the lymphatic system of the patient's body to move an excess of ions; and
   a controller configured to operate in an operational mode, wherein the controller operating in the operational mode is configured to:
      send a first electric test signal to the patient's body from the signal emitter of a first predetermined channel of the plurality of electric channels,
      measure the first electric test signal received by the signal receiver of the first predetermined channel of the plurality of electric channels,
      compare the measured first electric test signal and the sent first electric test signal,
      indicate the result of the comparison; and
      apply a first treatment electric signal to the patient's body based on the comparison from the electric signal emitter of the first predetermined channel.

2. The electrophysiology system according to claim 1, wherein apply a first treatment electric signal comprises:
   send the first treatment electric signal to the patient's body from the electric signal emitter of the first predetermined channel, and
   measure the first treatment electric signal received by the signal receiver of the first predetermined channel.

3. The electrophysiology system according to claim 1, wherein, at the operational mode, the controller is further configured to:
   send a second electric test signal to the patient's body from the signal emitter of a second predetermined channel of the plurality of electric channels, wherein the second predetermined channel is different from the first predetermined channel,
   measure the second electric test signal received by the signal receiver of the second predetermined channel of the plurality of electric channels,
   compare the measured second electric test signal and the sent second electric test signal,
   indicate the result of the comparison; and
   apply a second treatment electric signal to the patient's body based on the comparison from the electric signal emitter of the second predetermined channel.

4. The electrophysiology system according to claim 3, wherein the controller is configured to substantially simultaneously apply the first treatment electric signal and the second treatment electric signal.

5. The electrophysiology system according to claim 3, wherein the controller is configured to apply the second treatment electric signal with a predetermined delay after the first treatment electric signal.

6. The electrophysiology system according to claim 1, wherein the controller is further configured to operate in a preliminary mode, wherein the controller operating in the preliminary mode is configured to:
   send a query electric signal to the patient's body from the signal emitter of a predetermined electric channel of the plurality of electric channels,
   measure the query electric signal received by the electric signal receivers of the remaining electric channels of the plurality of electric channels, and
   identify the electric signal receivers with a measured query electric signal lower than a predetermined portion of the sent query electric signal.

7. The electrophysiology system according to claim 1, wherein the controller is further configured to activate one or more electric channels simultaneously thereby sending a respective electric signal to the patient's body via the electric signal emitter of each electric channel.

8. The electrophysiology system according to claim 1, wherein the controller is configured to successively activate the electric channels.

9. The electrophysiology system according to claim 1, further comprising a user interface and wherein the controller is configured to apply a signal selected via the user interface.

10. The electrophysiology system according to claim 1, wherein the electric signal source is configured to generate electric signals having an intensity equal to or lower than 300 µA.

11. The electrophysiology system according to claim 1, wherein the electric signal emitter and/or the electric signal receiver comprise an electrode pad comprising a pressing element having a protrusion on a side to be arranged on the patient's skin.

12. The electrophysiology system according to claim 11, wherein the pressing element comprises a coupling pin at an opposite side of the protrusion for removably coupling the electrode pad to an electrode socket.

13. The electrophysiology system according to claim 11, wherein the electrode pad comprises a ring comprising electrically conducting gel around the pressing element.

14. The electrophysiology system according to claim 11, wherein the protrusion comprises a diameter of about 1-10 mm.

15. A method for removing an excess of ions from a predetermined area of a patient's body, comprising:
   arranging a plurality of electric signal emitters and receivers on the patient's skin;
   selecting an operational mode, wherein the operational mode comprises:
      generating a first electric test signal;
      sending the first electric test signal from a signal emitter of a first channel of a plurality of electric channels;
      measuring the first electric test signal received by a signal receiver of the first channel of the plurality of electric channels;
      comparing the measured first electric test signal and the sent first electric test signal;

applying a first treatment electric signal from the electric signal emitter based on comparing the measured first electric test signal and the sent first electric test signal.

16. The method according to claim 15, wherein applying a first treatment electric signal comprises sending the first treatment electric signal from the electric signal emitter of the first predetermined channel and measuring the first treatment electric signal received by the signal receiver of the first predetermined channel.

17. The method according to claim 15, wherein the operational mode further comprises:
sending a second electric test signal from the signal emitter of a second predetermined channel of the plurality of electric channels, wherein the second predetermined channel is different from the first predetermined channel;
measuring the second electric test signal received by the signal receiver of the second predetermined channel of the plurality of electric channels;
comparing the measured second electric test signal and the sent second electric test signal; and
applying a second treatment electric signal based on the comparison from the electric signal emitter of the second predetermined channel.

18. The method according to claim 17, wherein the operational mode comprises delaying the second treatment electric signal after the first treatment electric signal.

19. The method according to claim 15, further comprising selecting a preliminary mode before the operational mode, wherein the preliminary mode comprises:
sending a query electric signal from the signal emitter of a predetermined electric channel of the plurality of electric channels;
measuring the query electric signal received by the electric signal receivers of the remaining electric channels of the plurality of electric channels, and
identifying the electric signal receivers with a measured query electric signal lower than a predetermined portion of the sent query electric signal.

20. An electrophysiology system for removing an excess of ions from a predetermined area of a patient's body, the system comprising:
an electric signal source configured to generate an electric signal having an intensity equal to or lower than 300 µA;
a plurality of electric channels connected to the electric signal source, wherein each channel comprises:
an electric signal emitter configured to send an electric signal generated by the electric signal source to a patient's body; and
an electric signal receiver configured to receive the electric signal sent from the electric signal emitter flowing through a part of the patient's body thereby creating a signal path that passes through the lymphatic system of the patient's body to move an excess of ions; and
a controller configured to operate in an operational mode and in a preliminary mode;
wherein the controller operating in the operational mode is configured to:
send a first electric test signal to the patient's body from the signal emitter of a first predetermined channel of the plurality of electric channels,
measure the first electric test signal received by the signal receiver of the first predetermined channel of the plurality of electric channels,
compare the measured first electric test signal and the sent first electric test signal,
indicate the result of the comparison,
apply a first treatment electric signal to the patient's body based on the comparison from the electric signal emitter of the first predetermined channel; and
wherein the controller operating in the preliminary mode is configured to:
send a query electric signal to the patient's body from the signal emitter of a predetermined electric channel of the plurality of electric channels,
measure the query electric signal received by the electric signal receivers of the remaining electric channels of the plurality of electric channels, and
identify the electric signal receivers with a measured query electric signal lower than a predetermined portion of the sent query electric signal.

* * * * *